US012544063B1

(12) United States Patent
Lim et al.

(10) Patent No.: US 12,544,063 B1
(45) Date of Patent: Feb. 10, 2026

(54) SURGICAL NEEDLE HOLDER AND METHODS OF USING THE SAME

(71) Applicant: Power Dental USA Inc., McHenry, IL (US)

(72) Inventors: Kyle Lim, McHenry, IL (US); Kang Ho Lim, Carpentersville, IL (US)

(73) Assignee: Power Dental U.S.A. Inc., McHenry, IL (US)

(*) Notice: Subject to any disclaimer, the term of this patent is extended or adjusted under 35 U.S.C. 154(b) by 0 days.

(21) Appl. No.: 19/183,357

(22) Filed: Apr. 18, 2025

(51) Int. Cl.
*A61B 17/06* (2006.01)

(52) U.S. Cl.
CPC .............................. *A61B 17/06061* (2013.01)

(58) Field of Classification Search
CPC B25B 7/14; B25B 7/16; A61B 17/062; A61B 17/06061; A61B 17/0483; A61B 17/2833; A61B 2017/2946; A61B 2017/2837; A61B 17/28–326
USPC ........... 606/148, 205–210; 81/315–341, 407, 81/411–412
See application file for complete search history.

(56) References Cited

U.S. PATENT DOCUMENTS

| | | | | | |
|---|---|---|---|---|---|
| 1,061,358 | A * | 5/1913 | Culver | B25B 7/14 | 81/322 |
| 2,652,832 | A * | 9/1953 | Castroviejo | A61B 17/062 | 606/147 |
| 4,949,717 | A * | 8/1990 | Shaw | A61B 17/062 | 606/174 |
| 5,236,436 | A * | 8/1993 | Koros | A61B 17/062 | 606/208 |
| 5,653,729 | A * | 8/1997 | Chappuis | A61B 17/062 | 606/205 |
| 6,270,134 | B1 * | 8/2001 | Lin | B25B 7/00 | 30/340 |
| 2002/0151931 | A1 * | 10/2002 | Tontarra | A61B 17/1611 | 606/205 |
| 2004/0254604 | A1 * | 12/2004 | Viart | A61B 17/2833 | 606/205 |
| 2006/0166535 | A1 * | 7/2006 | Brumfield | B25B 7/18 | 439/179 |
| 2007/0173814 | A1 * | 7/2007 | Hixson | A61B 18/1445 | 606/51 |
| 2008/0004637 | A1 * | 1/2008 | Klassen | A61B 17/128 | 606/157 |
| 2010/0318102 | A1 * | 12/2010 | Cheng | A61B 17/062 | 606/139 |
| 2017/0190025 | A1 * | 7/2017 | Li | B25B 7/14 | |

* cited by examiner

*Primary Examiner* — Kathleen S Holwerda
*Assistant Examiner* — Serenity A Miller
(74) *Attorney, Agent, or Firm* — Scherrer Patent & Trademark Law, P.C.; Stephen T. Scherrer; Monique A. Morneault

(57) ABSTRACT

Surgical needle holders comprise a pair of opposed needle gripping clamp jaws pivotally secured via a pivot, a pair of opposed handles, a pair of leaf spring sections extending from the opposed handles for biasing the needle gripping clamp jaws away from each other, and a rotating latch mechanism extending perpendicularly from one of the opposed handles and a contact surface extending from the other of the opposed handles for engaging and disengaging the same, thereby locking the pair of gripping clamp jaws in surface-to-surface arrangement. Methods of using the same are further provided.

19 Claims, 5 Drawing Sheets

SURGICAL NEEDLE HOLDER AND METHODS OF USING THE SAME

TECHNICAL FIELD

Surgical needle holders comprise a pair of opposed needle gripping clamp jaws pivotally secured via a pivot, a pair of opposed handles, a pair of leaf spring sections extending from the opposed handles for biasing the needle gripping clamp jaws away from each other, and a rotating latch mechanism extending perpendicularly from one of the opposed handles and a contact surface extending from the other of the opposed handles for engaging and disengaging the same, thereby locking the pair of gripping clamp jaws in surface-to-surface arrangement. Methods of using the same are further provided.

BACKGROUND

Surgical needle holders have been used in surgical procedures for many years. A needle holder, also called needle driver or needle forceps, is a surgical instrument similar to a hemostat, used by doctors and surgeons to hold and push a suturing needle when performing wound closure, ligation and other surgical procedures.

Being specialized forceps, the components of a typical needle holder are opposing jaws, a hinged joint connecting the opposing jaws, and opposing handles. Most needle holders also have some form of latching or locking mechanism that locks the handles together and allows a needle to clamp firmly between the opposing jaws, allowing the user to maneuver the needle through various tissues without having to keep squeezing the grip or handles. To maintain a firm grip on the needle, the jaws are often textured and short compared to the handles.

Most needle holders are designed to be gripped with the fingers and palm like scissors with a locking mechanism typically including a ratchet handle lock, specifically including a pair of perpendicularly disposed segments extending from the opposing handles having a plurality of parallel grooves that may align and mate together. Some needle holders are designed for a tweezers-like grip to allow finer more precise movements around delicate structures or narrow spaces. An example of such is the “Castroviejo” needle holder (named after Spanish American eye surgeon Ramón Castroviejo), which is commonly used in eye surgery, microsurgery and dental surgery.

The “Castroviejo” needle holder was described in U.S. Pat. No. 2,652,832, titled “Needle Holder,” which issued on Sep. 22, 1953. This apparatus includes a mechanism for latching and unlatching the same with the use of a lug extending from one of the handles for engaging a spring-loaded indent or groove extending from the other of the handles. Pressing the lug toward the indent or groove by squeezing the handles toward each other causes the lug to extend in a position to engage with the indent or groove, thereby locking the handles together and, thereby, opposing jaws. Pressing the handles further causes the lug to extend out of the groove, pushing the indent or groove out of its way until the lug moves past the indent or groove, whereby the lug may pass on the opposite side of the indent or groove when the handles are released.

The latching mechanism has changed very little over the past half century. Today, most Castroviejo-type needle holders include a pin or lug (the “latch”) that extends longitudinally (i.e., along the length of the needle holder from the end of the handles to the jaws thereof) from an inside surface of one of the pair of handles and a mating indent or groove on a longitudinally-extending spring-loaded surface (the “lock”) extending from an inside surface of the other of the pair of handles. The pin or lug of the latch contacts and presses past the spring-loaded surface of the lock until the pin or lug of the latch contacts the indent or groove on the surface of the lock, thereby locking the handles together. Continuous pressing of the handles toward each other causes the pin or lug of the latch to disengage from the indent or groove of the surface of the lock. The spring-loaded surface of the lock may be biased to its original position, and the pin or lug of the latch may slide past the surface of the lock on an opposite side thereof thereby allowing the handles to spread apart due to the biasing of leaf spring segments extending from each of the handles. This mechanism is very similar to what was disclosed in Ramon Castroviejo’s patent.

As noted above, the traditional Castroviejo-style latching mechanism comprises a longitudinally-disposed latch/lock mechanism that is very thin and quite flimsy because it is made from thin steel. As such, the positioning of the lock and/or the latch wears and moves over time thereby causing the lock and latch to misalign causing failure of the device to precisely hold needles in the jaws thereof. Specifically, misalignment of either the lock or the latch, or both, causes the function of the needle holder to fail. More specifically, once misaligned the jaws of the needle holder cannot hold onto sutures tightly, which may cause damage running the same through tissue during a surgical procedure. Damaged lock and/or latch components often require repair or simply are disposed of adding to costs and delays in using the same.

A need, therefore, exists for an improved needle holder instrument. Specifically, a need exists for an improved latching mechanism for a needle holder instrument that prevents movement of the components of the latching mechanism. More specifically, a need exists for an improved latching mechanism for a needle holder instrument that ensure that the needle holder jaws consistently hold sutures tightly.

Movement of the lock and/or the latch of the latching mechanism of traditional Castroviejo-style latching mechanisms may also vary the distance at which a user needs to squeeze the handles together to obtain a lock between the lock and the latch. Needle holder instruments are typically used by surgeons that require extremely precise and consistent instruments to ensure consistent, precise, and timely surgeries.

A need, therefore, exists for an improved latching mechanism for a needle holder instrument that ensures that the distance of movement of the handles when squeezed is consistent for locking the same. Specifically, a need exists for an improved latching mechanism that improves precision and timeliness of use. Moreover, a need exists for an improved latching mechanism for a needle holder instrument that leads to consistent and timely use thereof, especially during surgical procedures when longer surgery times can lead to worsening patient outcomes.

SUMMARY OF THE INVENTION

Surgical needle holders comprise a pair of opposed needle gripping clamp jaws pivotally secured via a pivot, a pair of opposed handles, a pair of leaf spring sections extending from the opposed handles for biasing the needle gripping clamp jaws away from each other, and a rotating latch mechanism extending perpendicularly from one of the opposed handles and a contact surface extending from the other of the opposed handles for engaging and disengaging the same, thereby locking the pair of gripping clamp jaws in surface-to-surface arrangement. Methods of using the same are further provided.

To this end, in an embodiment of the present invention, a surgical instrument is provided. The surgical instrument comprises: first and second clamp jaws; a pivot point between the first and second jaws; a first handle extending from the first jaw through the pivot point and a second handle extending from the second jaw through the pivot point, wherein the second handle comprises a first side and a second side laterally opposing the first side; a spring element biasing the first handle away from the second handle; a first arm extending roughly perpendicular from an inner surface of the first arm, wherein the first arm comprises a hook; and a contact surface running laterally across the inner surface of the second arm, wherein the contact surface engages the hook on the first arm when the first arm and the second arm are pushed together against the bias of the spring element.

In an embodiment, the spring element comprises a first leaf spring extending from the first handle and a second leaf spring extending from the second handle, wherein the first leaf spring and the second leaf spring are conjoined.

In an embodiment, the contact surface comprises a pin.

In an embodiment, the pin runs from a first side of the second handle to the second side of the second handle.

In an embodiment, the surgical instrument further comprises: a jaw disposed beneath the hook that is configured to move away from the hook to open a space beneath the hook.

In an embodiment, the jaw is biased toward the hook.

In an embodiment, the jaw is biased towards the hook via a spring.

In an embodiment, the contact surface is configured to enter the space beneath the hook after the jaw moves away from the hook to form the space beneath the hook.

In an embodiment, the jaw comprises a catch wherein the contact surface is configured to contact the catch and push the jaw away from the hook when the first and second handles are pushed together thereby opening the space beneath the hook.

In an embodiment, the contact surface is configured to enter the space beneath the hook after the contact surface contacts the catch and pushes the jaw away from the hook to open the space beneath the hook.

In an embodiment, the first handle and the second handle are configured to be unable to move apart from each other when the contact surface is disposed in the space beneath the hook.

In an embodiment, the clamp jaws are configured to lock together when the contact surface is disposed in the space beneath the hook.

In an embodiment, the surgical instrument further comprises: a jaw surface on an underside of the jaw.

In an embodiment, the contact surface is configured to open the space beneath the hook by pushing the first handle and the second handle closer together after the contact surface enters the space beneath the hook thereby allowing the jaw to move into the space beneath the hook after the space is vacated by the contact surface.

In an embodiment, the jaw moves into the space due to the jaw being biased toward the hook.

In an embodiment, the jaw is biased toward the hook via a spring.

In an embodiment, the contact surface is configured to travel over the jaw surface when after the jaw moves into the space under the hook when the first handle moves away from the second handle.

In an embodiment, the first handle and the second handle are biased away from each other.

In an embodiment, the first handle and the second handle are biased away from each other via one or more leaf springs.

In an embodiment, the first arm comprises an arm pivot, wherein the first arm is configured to rotate on the arm pivot alternately toward the second handle and away from the second handle.

It is, therefore, an advantage and objective of the present invention to provide an improved needle holder instrument.

Specifically, it is an advantage and objective of the present invention to provide an improved latching mechanism for a needle holder instrument that prevents movement of the components of the latching mechanism.

More specifically, it is an advantage and objective of the present invention to provide an improved latching mechanism for a needle holder instrument that ensure that the needle holder jaws consistently hold sutures tightly.

Moreover, it is an advantage and objective of the present invention to provide an improved latching mechanism for a needle holder instrument that ensures that the distance of movement of the handles when squeezed is consistent for locking the same.

Specifically, it is an advantage and objective of the present invention to provide an improved latching mechanism that improves precision and timeliness of use.

More specifically, it is an advantage and objective of the present invention to provide an improved latching mechanism for a needle holder instrument that leads to consistent and timely use thereof, especially during surgical procedures when longer surgery times can lead to worsening patient outcomes.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE PRESENTLY PREFERRED EMBODIMENTS

Surgical needle holders comprise a pair of opposed needle gripping clamp jaws pivotally secured via a pivot, a pair of opposed handles, a pair of leaf spring sections extending from the opposed handles for biasing the needle gripping clamp jaws away from each other, and a rotating latch mechanism extending perpendicularly from one of the opposed handles and a contact surface extending from the other of the opposed handles for engaging and disengaging the same, thereby locking the pair of gripping clamp jaws in surface-to-surface arrangement. Methods of using the same are further provided.

Figure 1:
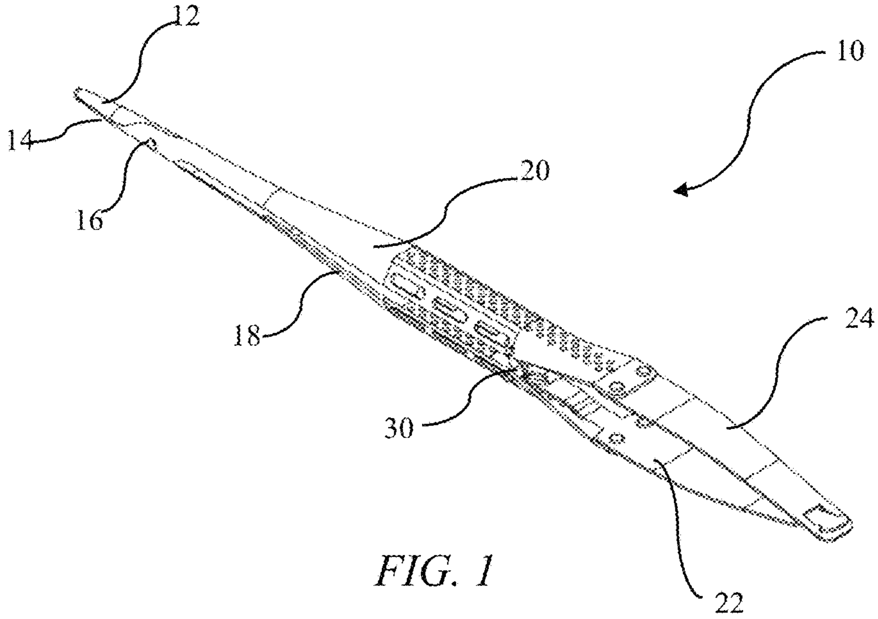
FIG. 1 illustrates a perspective view of a needle holder instrument with a latching mechanism in a latched configuration in an embodiment of the present invention.

Now referring to the figures, wherein like numerals refer to like parts, FIG. 1 illustrates a perspective view of a needle holder instrument 10 in an embodiment of the present invention. The needle holder instrument 10 comprises a pair of clamp jaws 12, 14 that open and close around pivot 16. First and second handles 18, 20 extend from the pivot 16 to control the opening and closing of the clamp jaws 12, 14. Specifically, first handle 18 extends from clamp jaw 12 through pivot 16 and second handle 20 extends from clamp jaw 14 through pivot 16.

Figure 3:
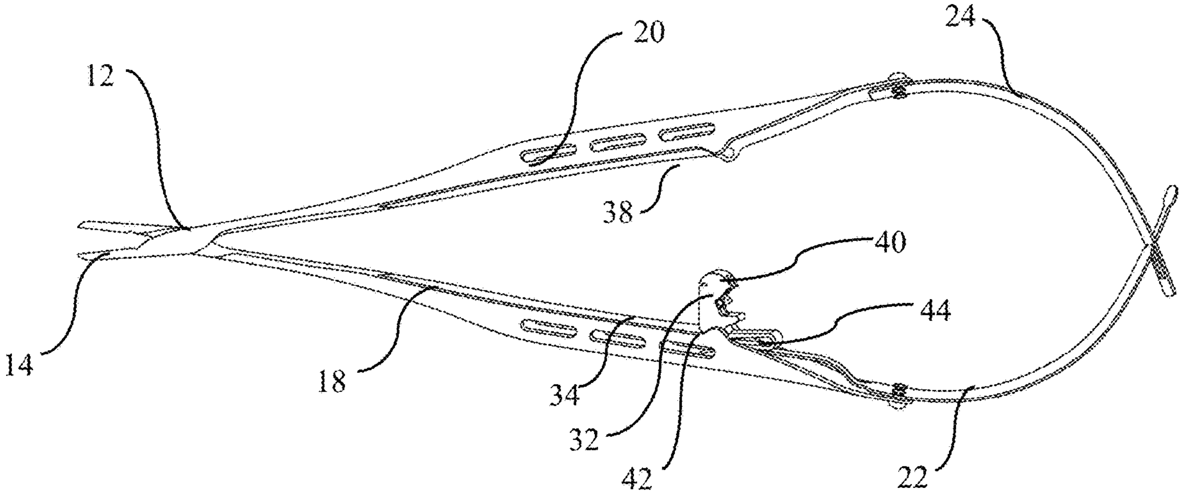
FIG. 3 illustrates a side view of a needle holder instrument with a latching mechanism in an unlatched configuration in an embodiment of the present invention.

A first leaf spring 22 may extend from an end of the first handle 18 which may connect with a second leaf spring 24, which may extend from an end of the second handle 20. The first and second leaf springs 22, 24 may bias the first and second handles 18, 20 away from each other, thereby biasing the clamp jaws 12, 14 in an open configuration, as illustrated in FIG. 3. Squeezing or otherwise pushing the first and second handles 18, 20 toward each other may close the clamp jaws 12, 14. In a preferred embodiment, the clamp jaws 12, 14 are configured to hold needles and sutures for use in surgical procedures. However, it should be noted that the mechanisms described herein may be used for other instruments as well where clamp jaws are desired to be locked together as described herein.

A latch/lock mechanism 30 may be disposed between the first and second handles 18, 20 to provide a locking mechanism to maintain the handles together, against the bias of the first and second leaf springs 22, 24, thereby maintaining the clamp jaws 12, 14 in a closed and rigidly locked configuration. This may be useful in holding needles and sutures during surgery and for other like needs.

Figure 2:
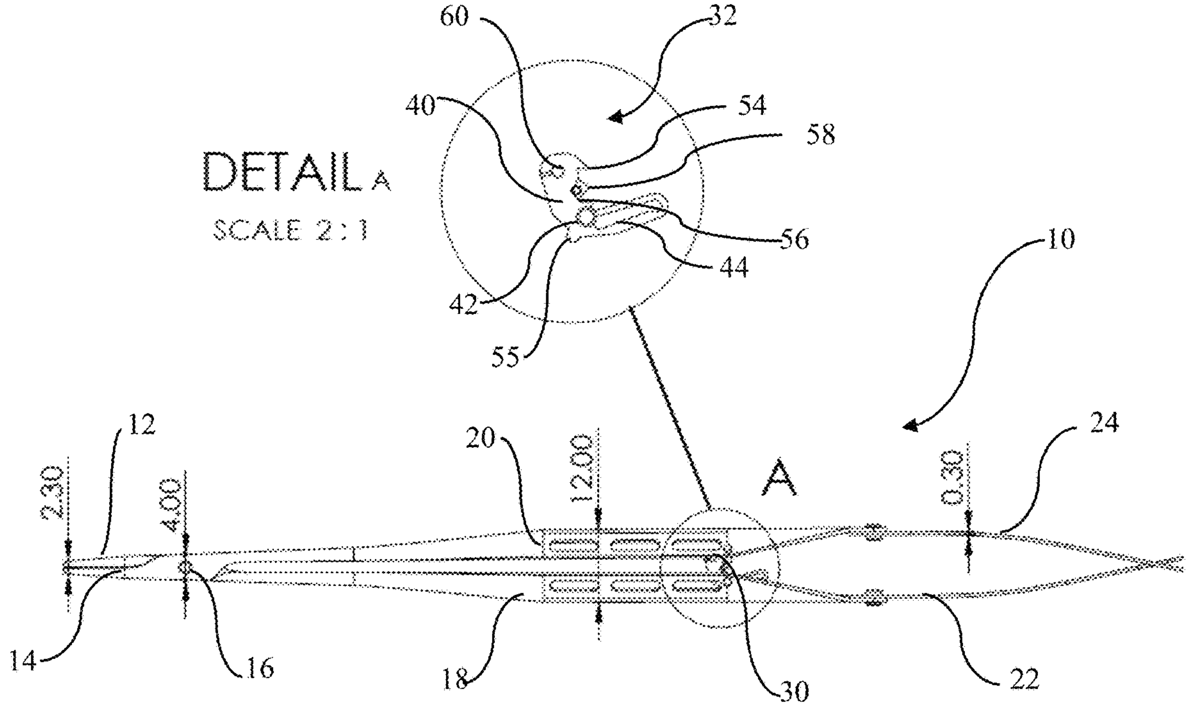
FIG. 2 illustrates a side view of a needle holder instrument with a latching mechanism in a latched configuration in an embodiment of the present invention.

The latch/lock mechanism 30 may comprise a rotating latch component 32 pivotally disposed on or adjacent an inside surface 34 of the first handle 18 and a static lock component 36 disposed on or adjacent an inside surface 38 of the second handle 20. The latch component 32 and the lock component 36 may be aligned together such that, when brought together, as shown in FIG. 2 and further as described and shown herein with respect to FIGS. 3-8, they engage with each other, thereby locking the first handle and the second handle in close proximity and, thus, locking the clamp jaws 12, 14 rigidly.

Figure 9A:
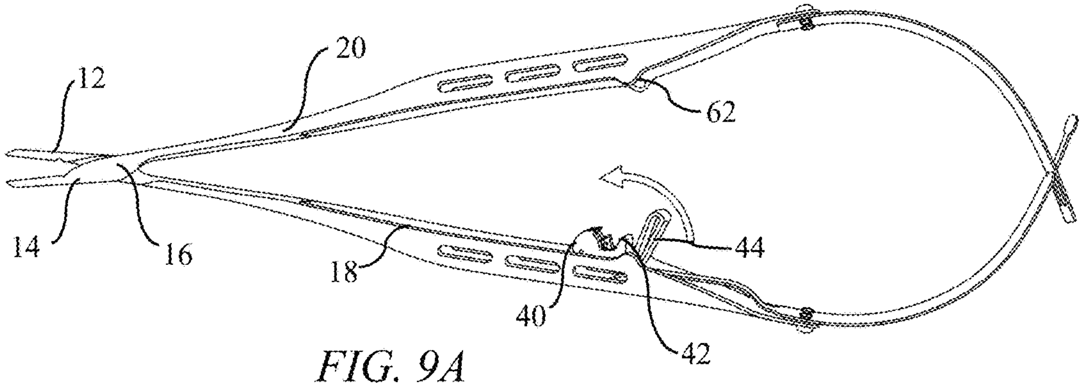
FIGS. 9A-9C illustrate side views of a needle holder instrument showing the needle holder in an unlatchable configuration in an embodiment of the present invention.
Figure 9B:
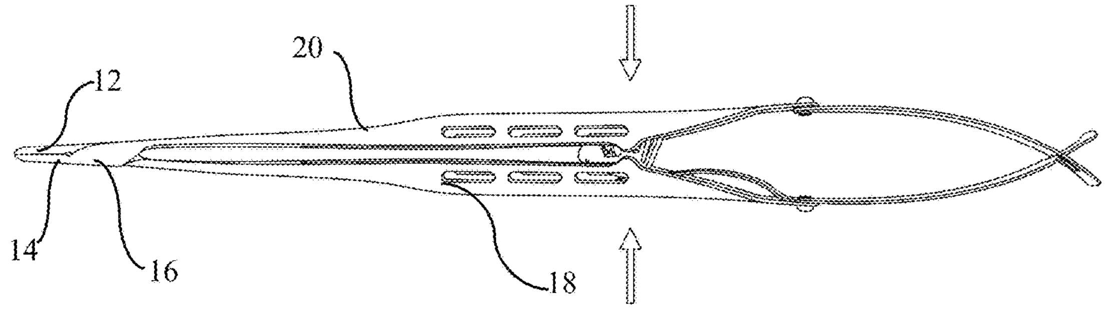
Figure 9C:
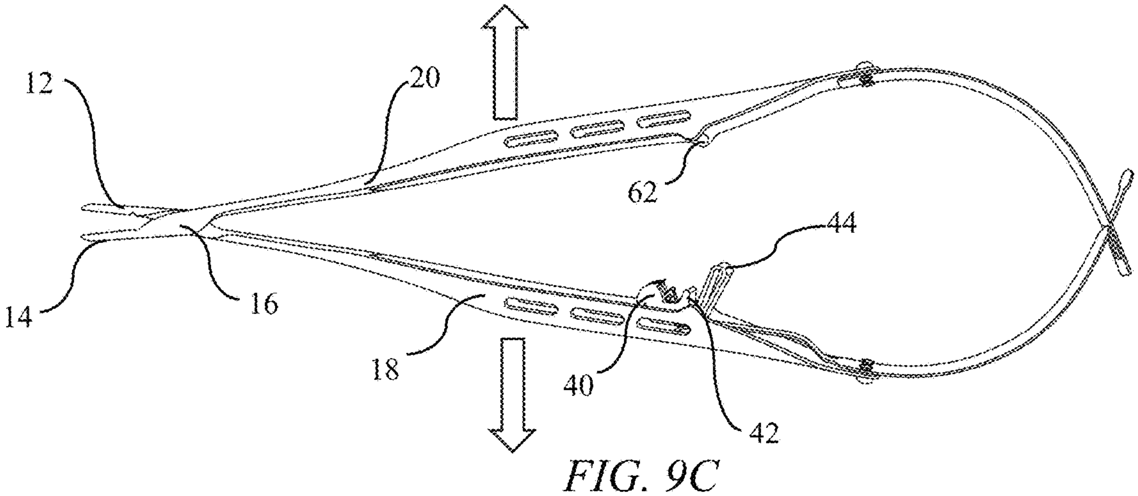

The latch component 32 may preferably comprise a first arm 40 extending from an arm pivot 42 and a second arm 44 extending from the arm pivot 42 at roughly perpendicular to the first arm 40. The first arm 40 and the second arm 44 may rotate about the arm pivot 42 as illustrated in FIG. 4, namely so that either the first arm 40 or the second arm 44 (as shown in FIGS. 9A-9C) may extend roughly perpendicular from the inner surface 34 of the first handle 18.

Figure 4:
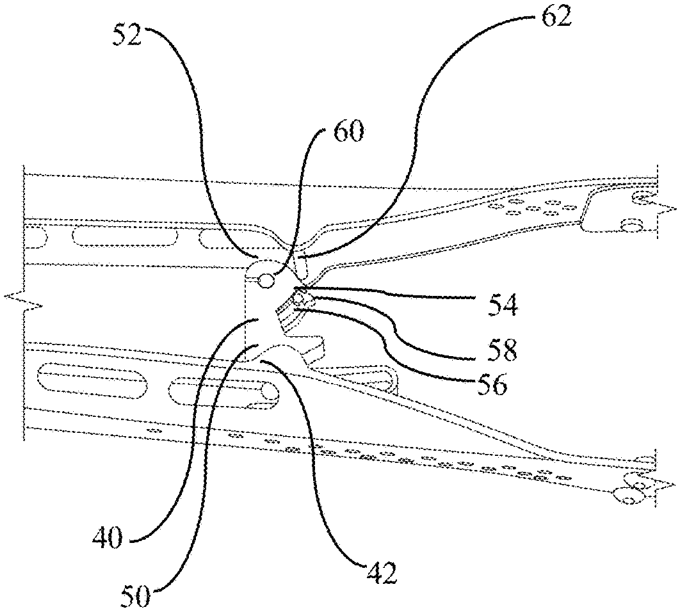
FIG. 4 illustrates a side view of a needle holder instrument with a latching mechanism in a partially latched configuration in an embodiment of the present invention.
Figure 5:
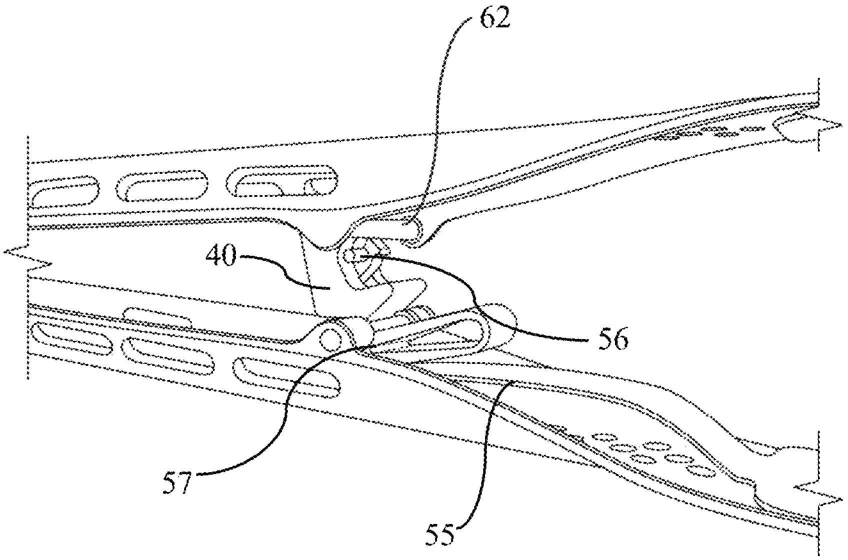
FIG. 5 illustrates a side view of a needle holder instrument with a latching mechanism in a further partially latched configuration in an embodiment of the present invention.
Figure 6:
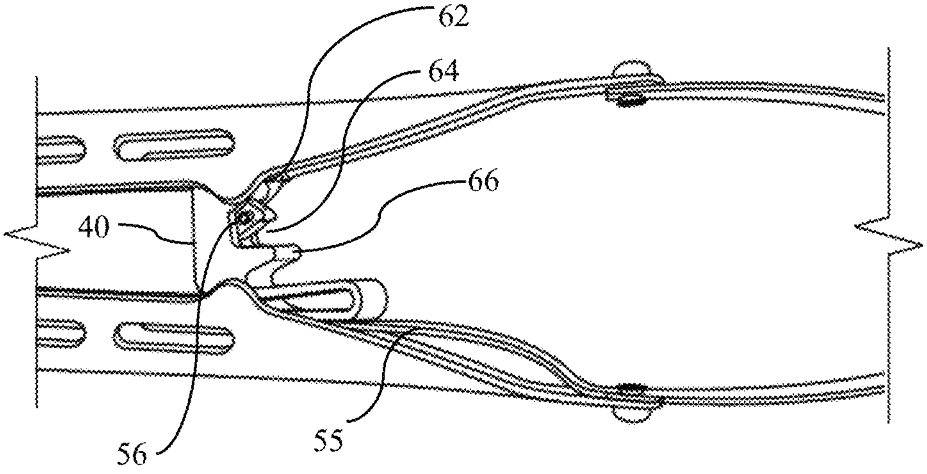
FIG. 6 illustrates a side view of a needle holder instrument with a latching mechanism in a fully latched configuration in an embodiment of the present invention.

As shown in FIG. 4, the first arm 40 may comprise a first end 50 that is adjacent the arm pivot 42 and a second end 52. On or near the second end 52 may be a hook element 54 and a lower jaw element 56 having a catch 58. The lower jaw element 56 may be spring-loaded and rotate about pivot 60, thereby biased toward the hook element 54. Pressing down on the catch 58 may push the lower jaw element 56 downwardly and rotate the lower jaw element 56 away from the hook element 54. This may be accomplished via the lock component 36, which may be a horizontally-disposed pin 62 extending laterally from one side of the second handle 20 to a second side of the second handle 20 at or near the inside surface 38 of the second handle 20. As the first handle 18 and the second handle 20 are pressed toward each other against the bias formed by the first and second leaf springs 22, 24, respectively, the horizontally disposed pin 62 may be pressed toward the latch component 32, as shown in FIG. 4. As the first and second handles move closer together, the pin 62 may act as a contact surface and engage the catch 58, which may push the lower jaw element 56 away from the hook element 54, as illustrated in FIG. 5. Once sufficiently clear from the hook element 54, the lower jaw element 56 may open the space into which the pin 62 may engage under the hook element 54, as illustrated in FIG. 6. A leaf spring 55 may engage a heal 57 on the latch component 32, as illustrated in FIGS. 5 and 6, and may bias the first arm 40 toward the pin 62, aiding in ensuring that the pin 62 is disposed in the space beneath the hook element 54 when the lower jaw element 56 has moved and the space beneath the hook element 54 is opened.

When the pin 62 is engaged beneath the hook element 54, it may thereby lock the first and second handles 18, 20, respectively, together preventing movement of the same away from each other against the bias caused by the first and second leaf springs 22, 24, respectively. When the first and second handles 18, 20, respectively, are locked together in such a manner, the clamp jaws 12, 14 may also be locked together (as shown in FIG. 2), such as when holding a needle and suture between the clamp jaws 12, 14, respectively, for use in a surgical procedure. A user, such as a surgeon, for example, may thus then release the pressure upon the first and second handles 18, 20, respectively, and the jaws 12, 14 may remain locked together, thereby holding a needle and suture therein for use in suturing. The latch/lock mechanism 30, as described and shown herein, may provide a rigid and strong fixed bar mechanism that extends perpendicularly between the first and second handles 18, 20, respectively. Thus, the latch/lock mechanism 30 may have great tensile strength, especially when compared to prior art locking mechanisms as described herein, thereby better withstanding the daily grind of surgery.

Figure 7:
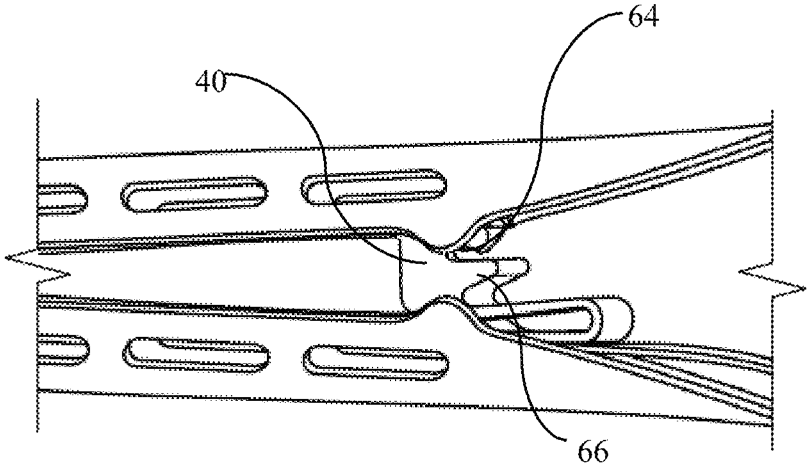
FIG. 7 illustrates a side view of a needle holder instrument with a latching mechanism in a partially unlatched configuration in an embodiment of the present invention.

The bias of the lower jaw element 56 may push the lower jaw element 56 against the pin 62 when the pin 62 is disposed beneath the hook element 54; however, the lower jaw element 56 may be prevented from returning to its initial position under the hook element 54 until the pin 62 is clear therefrom. A user may clear the pin 62 from under the hook element 54 by further pushing the first and second handles 18, 20, respectively, together, as illustrated in FIG. 7. Thus, the pin 62 may further descend into a corner 64 formed at the intersection between the first arm 40 and an elongated bar 66 that may extend from the first end 50 of the first arm 40. Once the pin 62 is disposed in the corner 64, it may be sufficiently clear from the hook element 54 to allow the lower jaw element 56 (being biased toward the hook element 54) to rotate and return to its position beneath the hook element 54.

Figure 8:
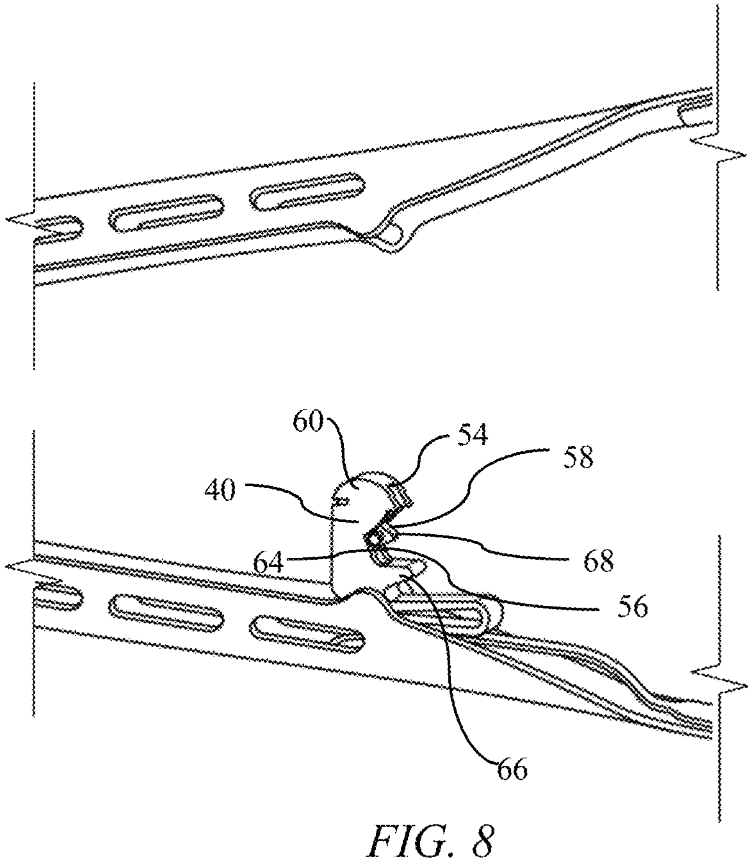
FIG. 8 illustrates a side view of a needle holder instrument with a latching mechanism in a fully unlatched configuration in an embodiment of the present invention.

The lower jaw element 56 may have a lower surface 68, as shown in FIG. 8, over which the pin 62 may travel when a user releases the first and second handles 18, 20, respectively, thereby allowing the first and second leaf springs 22, 24 to bias the first and second handles 18, 20, respectively, apart from each other. Because the lower jaw element 56 may now be biased in position beneath the hook element 54, the pin 62 may travel over the lower surface 68 of the lower jaw element 56 and past the catch 58 when the first and second handles 18, 20 move away from each other, which may ensure that the pin 62 remains clear of the hook element 54 as it travels. Therefore, the pin 62 may be released from the first arm 40, allowing the first and second handles 18, 20, respectively, to fully move away from each other, as shown in FIG. 8, thereby opening clamp jaws 12, 14.

FIGS. 9A, 9B, and 9C illustrate a sequence whereby the needle holder instrument 10 may be used in a non-locking or unlatchable capacity by rotating the first arm 40 away from a perpendicular position via the arm pivot 42, thereby causing the second arm 44 to rotate away from the inside surface 34 of the first handle 18. The second arm 44 may have no elements which may catch or engage the pin 62, and therefore the first and second handles 18, 20, respectively, may freely open and close without locking. Once a user wishes to lock the first and second handles 18, 20 together and, thus, the clamp jaws 12, 14, the user may simply rotate the first arm 40 so that it is perpendicular to the first handle 18 and aligned with the pin 62, as described above.

Preferably, the needle holder instrument 10 and components thereof are made of steel, although the present invention should not be limited as described and may be made from any material apparent to one of ordinary skill in the art. The needle holder instrument 10 and/or, preferably, the latch/lock mechanism 30 may further be titanium-coated to reinforce the same and ensure that the components thereof remain in their proper shapes and rigidity, thereby extending the longevity thereof.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

What is claimed is:

1. A surgical instrument comprising: first and second clamp jaws; the first and second clamp jaws open and close about a pivot point; a first handle extending from the first jaw through the pivot point and a second handle extending from the second jaw through the pivot point, wherein the second handle comprises a first side and a second side laterally opposing the first side; a spring element biasing the first handle away from the second handle; a first arm extending roughly perpendicular from an inner surface of the first handle, wherein the first arm comprises a hook; a contact surface running laterally across an inner surface of the second handle, wherein the contact surface engages the hook on the first arm when the first arm and the second arm are pushed together against the bias of the spring element; a jaw disposed beneath the hook that is configured to move away from the hook to open a space beneath the hook, wherein the jaw comprises a catch, wherein the contact surface is configured to contact the catch and push the jaw away from the hook when the first and second handles are pushed together thereby opening the space beneath the hook, wherein the contact surface is configured to enter the space beneath the hook after the contact surface contacts the catch and pushes the jaw away from the hook to open the space beneath the hook; and a jaw surface on an underside of the jaw, wherein the contact surface is configured to travel over the jaw surface after the jaw moves into the space beneath the hook when the first handle moves away from the second handle.

2. The surgical instrument of claim 1, wherein the spring element comprises a first leaf spring extending from the first handle and a second leaf spring extending from the second handle, wherein the first leaf spring and the second leaf spring are conjoined.

3. The surgical instrument of claim 1, wherein the contact surface comprises a pin.

4. The surgical instrument of claim 3, wherein the pin runs from the first side of the second handle to the second side of the second handle.

5. The surgical instrument of claim 1, wherein the jaw is biased toward the hook.

6. The surgical instrument of claim 5, wherein the jaw is biased towards the hook via a spring.

7. The surgical instrument of claim 1, wherein the first handle and the second handle are configured to be unable to move apart from each other when the contact surface is disposed in the space beneath the hook.

8. The surgical instrument of claim 7, wherein the clamp jaws are configured to lock together when the contact surface is disposed in the space beneath the hook.

9. The surgical instrument of claim 1, wherein the contact surface is configured to open the space beneath the hook by pushing the first handle and the second handle closer together after the contact surface enters the space beneath the hook thereby allowing the jaw to move into the space beneath the hook after the space is vacated by the contact surface.

10. The surgical instrument of claim 1, wherein the jaw moves into the space due to the jaw being biased toward the hook.

11. The surgical instrument of claim 10, wherein the jaw is biased toward the hook via a spring.

12. The surgical instrument of claim 1, wherein the spring element comprises one or more leaf springs.

13. The surgical instrument of claim 1, wherein the first arm comprises an arm pivot, wherein the first arm is configured to rotate on the arm pivot alternately toward the second handle and away from the second handle.

14. A method of using a surgical instrument comprising the steps of: providing the surgical instrument, wherein the surgical instrument comprises: first and second clamp jaws, the first and second clamp jaws open and close about a pivot point, a first handle extending from the first jaw through the pivot point and a second handle extending from the second jaw through the pivot point, wherein the second handle comprises a first side and a second side laterally opposing the first side; a first spring element biasing the first handle away from the second handle; a first arm extending roughly perpendicular from an inner surface of the first handle, wherein the first arm comprises a hook; a contact surface running laterally across an inner surface of the second handle, wherein the contact surface engages the hook on the first arm when the first arm and the second arm are pushed together against the bias of the first spring element; a jaw disposed beneath the hook that is configured to move away from the hook to open a space beneath the hook, wherein the jaw comprises a catch, wherein the contact surface is configured to contact the catch and push the jaw away from the hook when the first and second handles are pushed together thereby opening the space beneath the hook, wherein the contact surface is configured to enter the space beneath the hook after the contact surface contacts the catch and pushes the jaw away from the hook to open the space beneath the hook; and a jaw surface on an underside of the jaw, wherein the contact surface is configured to travel over the jaw surface after the jaw moves into the space beneath the hook when the first handle moves away from the second handle; pushing the first handle toward the second handle against the bias of the first spring element; pushing the jaw away from the hook with the contact surface and opening up the space beneath the hook; engaging the contact surface with the hook of the first arm when the contact surface is disposed within the space beneath the hook thereby preventing the first handle from moving away from the second handle.

15. The method of claim 14, further comprising the steps of: pushing the first handle further toward the second handle against the bias of the first spring element after the contact surface is disposed within the space beneath the hook causing the contact surface to vacate the space beneath the hook; and moving the jaw into the space beneath the hook vacated by the contact surface; allowing the first handle to move away from the second handle via the bias of the first spring element and causing the contact surface to travel over the jaw surface after the jaw has moved into the space beneath the hook.

16. The method of claim 14, wherein the jaw is biased toward the hook via a second spring element.

17. The method of claim 14, wherein the first spring element is a leaf spring.

18. The method of claim 14, wherein the first arm comprises an arm pivot, wherein the first arm is configured to rotate on the arm pivot alternately toward the second handle to a first position and away from the second handle to a second position.

19. The method of claim 18, further comprising the step of: rotating the first arm to the first position and allowing the first arm to engage the contact surface; and rotating the first arm to the second position and preventing the first arm from engaging with the contact surface.

* * * * *